United States Patent
Samuelson et al.

(10) Patent No.: US 6,464,683 B1
(45) Date of Patent: *Oct. 15, 2002

(54) TRILAYER, EXTRUDED MEDICAL TUBING AND MEDICAL DEVICES INCORPORATING SUCH TUBBING

(75) Inventors: Christine M. Samuelson; Sarah J. Krieger, both of Plymouth, MN (US)

(73) Assignee: Schneider (USA) Inc., Plymouth, MN (US)

( * ) Notice: Subject to any disclaimer, the term of this patent is extended or adjusted under 35 U.S.C. 154(b) by 50 days.

This patent is subject to a terminal disclaimer.

(21) Appl. No.: 09/695,514

(22) Filed: Oct. 24, 2000

Related U.S. Application Data

(63) Continuation of application No. 09/014,789, filed on Jan. 28, 1998, now Pat. No. 6,165,166.
(60) Provisional application No. 60/044,879, filed on Apr. 25, 1997.

(51) Int. Cl.$^7$ .................... A61M 25/00; A61M 29/00
(52) U.S. Cl. ................................. 604/524; 604/96.01
(58) Field of Search .................. 604/96.01, 264, 604/524–527

(56) References Cited

U.S. PATENT DOCUMENTS

| | | | |
|---|---|---|---|
| 3,561,493 A | 2/1971 | Maillard et al. | 138/141 |
| 3,618,614 A | 11/1971 | Flynn | 128/348 |
| 3,695,921 A | 10/1972 | Shepherd et al. | 117/72 |
| 3,814,137 A | 6/1974 | Martinez | 138/103 |
| 3,890,976 A | 6/1975 | Bazell et al. | 128/351 |
| 4,157,932 A | 6/1979 | Hirata | 156/310 |
| 4,171,416 A | 10/1979 | Motegi et al. | 526/245 |
| 4,211,741 A | 7/1980 | Ostoich | 264/173 |
| 4,265,848 A | 5/1981 | Rüsch | 264/130 |
| 4,282,876 A | 8/1981 | Flynn | 128/349 R |
| 4,323,071 A | 4/1982 | Simpson et al. | 128/343 |
| 4,335,723 A | 6/1982 | Patel | 128/349 B |
| 4,413,989 A | 11/1983 | Schjeldahl et al. | 604/96 |
| 4,596,563 A | 6/1986 | Pande | 604/264 |
| 4,597,755 A | 7/1986 | Samson et al. | 604/96 |
| 4,627,844 A | 12/1986 | Schmitt | 604/264 |
| 4,636,346 A | 1/1987 | Gold et al. | 264/139 |
| 4,646,719 A | 3/1987 | Neuman et al. | 128/1 D |
| 4,702,252 A | 10/1987 | Brooks et al. | 128/344 |
| 4,707,389 A | 11/1987 | Word | 428/36 |

(List continued on next page.)

FOREIGN PATENT DOCUMENTS

| | | |
|---|---|---|
| CA | 2078201 A1 | 12/1992 |
| EP | 0 277 368 A1 | 8/1988 |
| EP | 0 279 959 B1 | 8/1988 |
| EP | 0 298 634 A1 | 1/1989 |
| EP | 0 351 687 A2 | 1/1990 |
| EP | 0 358 117 B1 | 3/1990 |
| EP | 0 380 102 A1 | 8/1990 |
| EP | 0 420 488 A1 | 4/1991 |
| EP | 0 436 501 B1 | 7/1991 |
| EP | 0 452 123 A1 | 10/1991 |

*Primary Examiner*—Sharon Kennedy
(74) *Attorney, Agent, or Firm*—Crompton, Seager & Tufte, LLC

(57) ABSTRACT

The present invention provides a length of trilayer, extruded, medical tubing comprising an outer layer, a core layer, and an intermediate tie layer. The outer layer comprises a polymer that is directly bondable, while the core layer comprises a lubricious polymer. The core layer thus defines a lumen that exhibits the desired characteristics, i.e., low friction for the advancement of a guidewire or catheter through the lumen without comprising the strength and stiffness that is desirable in tubing that is to be used in medical devices. Additionally, the tubing is easily coextruded and yet, is not subject to delamination, thus providing the added advantage of providing a reduction in the overall cost of manufacture.

23 Claims, 3 Drawing Sheets

U.S. PATENT DOCUMENTS

| | | | |
|---|---|---|---|
| 4,729,914 A | 3/1988 | Kliment et al. | 428/36 |
| 4,744,366 A | 5/1988 | Jang | 128/344 |
| 4,762,129 A | 8/1988 | Bonzel | 128/344 |
| 4,763,654 A | 8/1988 | Jang | 128/344 |
| 4,769,099 A | 9/1988 | Therriault et al. | 156/230 |
| 4,775,371 A | 10/1988 | Mueller, Jr. | 604/280 |
| 4,776,849 A | 10/1988 | Shinno et al. | 604/283 |
| 4,782,834 A | 11/1988 | Maguire et al. | 128/344 |
| 4,820,349 A | 4/1989 | Saab | 128/344 |
| 4,863,449 A | 9/1989 | Therriault et al. | 604/352 |
| 4,900,314 A | 2/1990 | Quackenbush | 604/282 |
| 4,906,244 A | 3/1990 | Pinchuk et al. | 606/194 |
| 4,921,483 A | 5/1990 | Wijay et al. | 604/96 |
| 4,923,450 A | 5/1990 | Maeda et al. | 604/265 |
| 4,940,179 A | 7/1990 | Soni | 228/56.3 |
| 4,955,895 A | 9/1990 | Sugiyama et al. | 606/194 |
| 4,960,410 A | 10/1990 | Pinchuk | 604/96 |
| 4,976,690 A | 12/1990 | Solar et al. | 604/96 |
| 4,976,720 A | 12/1990 | Machold et al. | 606/194 |
| 4,981,478 A | 1/1991 | Evard et al. | 604/282 |
| 4,994,018 A | 2/1991 | Saper | 600/18 |
| 4,994,032 A | 2/1991 | Sugiyama et al. | 604/96 |
| 4,994,047 A | 2/1991 | Walker et al. | 604/264 |
| 5,006,119 A | 4/1991 | Acker et al. | 606/27 |
| 5,026,377 A | 6/1991 | Burton et al. | 606/108 |
| 5,035,694 A | 7/1991 | Kasprzyk et al. | 606/27 |
| 5,041,089 A | 8/1991 | Mueller et al. | 604/96 |
| 5,041,100 A | 8/1991 | Rowland et al. | 604/265 |
| 5,047,045 A | 9/1991 | Arney et al. | 606/194 |
| 5,059,269 A | 10/1991 | Hu et al. | 156/244.11 |
| 5,063,018 A | 11/1991 | Fontirroche et al. | 264/514 |
| 5,078,727 A | 1/1992 | Hannam et al. | 606/194 |
| 5,085,649 A | 2/1992 | Flynn | 604/282 |
| 5,100,381 A | 3/1992 | Burns | 604/96 |
| 5,100,386 A | 3/1992 | Inoue | 604/103 |
| 5,114,423 A | 5/1992 | Kasprzyk et al | 606/27 |
| 5,120,323 A | 6/1992 | Shockey et al. | 604/282 |
| 5,147,315 A | 9/1992 | Weber | 604/164 |
| 5,195,969 A | 3/1993 | Wang et al. | 604/996 |
| 5,195,971 A | 3/1993 | Sirhan | 604/96 |
| 5,221,270 A | 6/1993 | Parker | 604/282 |
| 5,234,416 A | 8/1993 | Macaulay et al. | 604/282 |
| 5,250,069 A | 10/1993 | Nobuyoshi et al. | 606/192 |
| 5,254,090 A | 10/1993 | Lombardi et al. | 604/96 |
| 5,267,959 A | 12/1993 | Forman | 604/103 |
| 5,270,086 A | 12/1993 | Hamlin | 428/35.2 |
| 5,272,012 A | 12/1993 | Opolski | 428/423.1 |
| 5,279,560 A | 1/1994 | Morrill et al. | 604/96 |
| 5,290,230 A | 3/1994 | Ainsworth et al. | 604/96 |
| 5,290,306 A | 3/1994 | Trotta et al. | 606/194 |
| 5,304,134 A | 4/1994 | Kraus et al. | 604/96 |
| 5,338,299 A | 8/1994 | Barlow | 604/96 |
| 5,348,536 A | 9/1994 | Young et al. | 604/43 |
| 5,356,709 A | 10/1994 | Woo et al. | 428/376 |
| 5,383,853 A | 1/1995 | Jung et al. | 604/96 |
| 5,397,306 A | 3/1995 | Nobuyoshi et al. | 604/96 |
| 5,403,292 A | 4/1995 | Ju | 604/282 |
| 5,405,338 A | 4/1995 | Kranys | 604/282 |
| 5,409,495 A | 4/1995 | Osborn | 606/108 |
| 5,423,754 A | 6/1995 | Cornelius et al. | 604/103 |
| 5,425,712 A | 6/1995 | Goodin | 604/96 |
| 5,439,454 A | 8/1995 | Lo et al. | 604/264 |
| 5,460,608 A | 10/1995 | Lodin et al. | 604/96 |
| 5,478,320 A | 12/1995 | Trotta | 604/96 |
| 5,484,444 A | 1/1996 | Braunschweiler et al. | 606/108 |
| 5,499,973 A | 3/1996 | Saab | 604/96 |
| 5,501,759 A | 3/1996 | Forman | 156/272.8 |
| 5,514,236 A | 5/1996 | Avellant et al. | 156/154 |
| 5,527,281 A | 6/1996 | Haas | 604/103 |
| 5,533,985 A | 7/1996 | Wang | 604/264 |
| 5,538,510 A | 7/1996 | Fontirroche et al. | 604/265 |
| 5,545,151 A | 8/1996 | O'Connor et al. | 604/265 |
| 5,549,552 A | 8/1996 | Peters et al. | 604/282 |
| 5,558,737 A | 9/1996 | Brown et al. | 156/172 |
| 5,562,127 A | 10/1996 | Fanselow et al. | 138/137 |
| 5,571,089 A | 11/1996 | Crocker | 604/102 |
| 5,620,649 A | 4/1997 | Trotta | 264/515 |
| 5,643,209 A | 7/1997 | Fugoso et al. | 604/96 |
| 5,653,691 A | 8/1997 | Rupp et al. | 604/96 |
| 5,676,659 A | 10/1997 | McGurk | 604/282 |
| 5,728,063 A | 3/1998 | Preissman et al. | 604/96 |
| 5,728,088 A | 3/1998 | Magruder et al. | 604/892.1 |
| 5,733,400 A | 3/1998 | Gore et al. | 156/158 |
| 5,749,852 A | 5/1998 | Schwab et al. | 604/96 |
| 5,792,814 A | 8/1998 | Oishi et al. | 525/119 |
| 5,797,877 A | 8/1998 | Hamilton et al. | 604/96 |
| 5,820,594 A | 10/1998 | Fontirroche et al. | 604/96 |
| 5,824,173 A | 10/1998 | Fontirroche et al. | 156/86 |
| 5,837,313 A | 11/1998 | Ding et al. | 427/2.21 |
| 5,843,032 A | 12/1998 | Kastenhofer | 604/96 |
| 5,853,400 A | 12/1998 | Samson | 604/282 |
| 5,961,765 A | 10/1999 | Kastenhofer | 156/244.13 |
| 6,027,477 A | 2/2000 | Kastenhofer | 604/96 |
| 6,165,166 A | 12/2000 | Samuelson et al. | 604/524 |

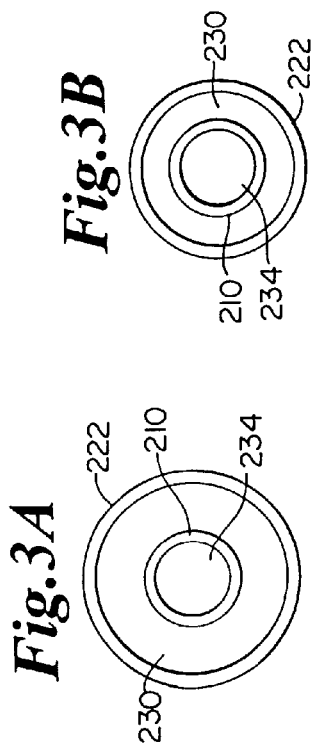
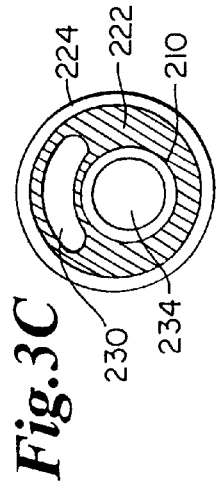
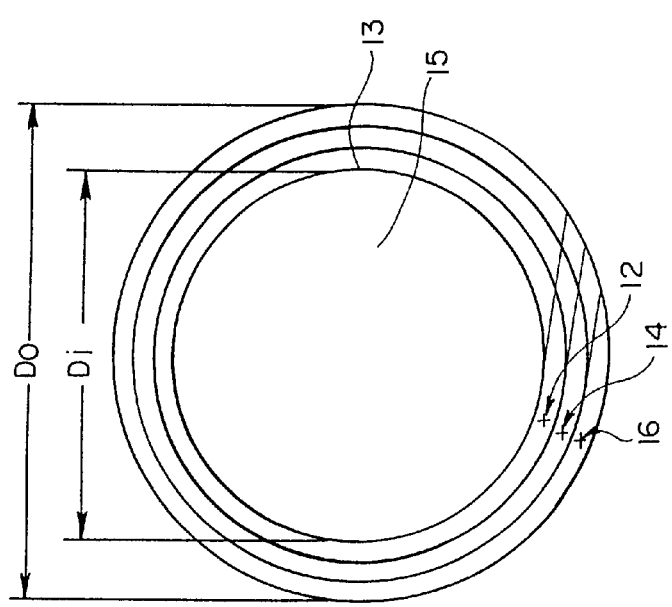
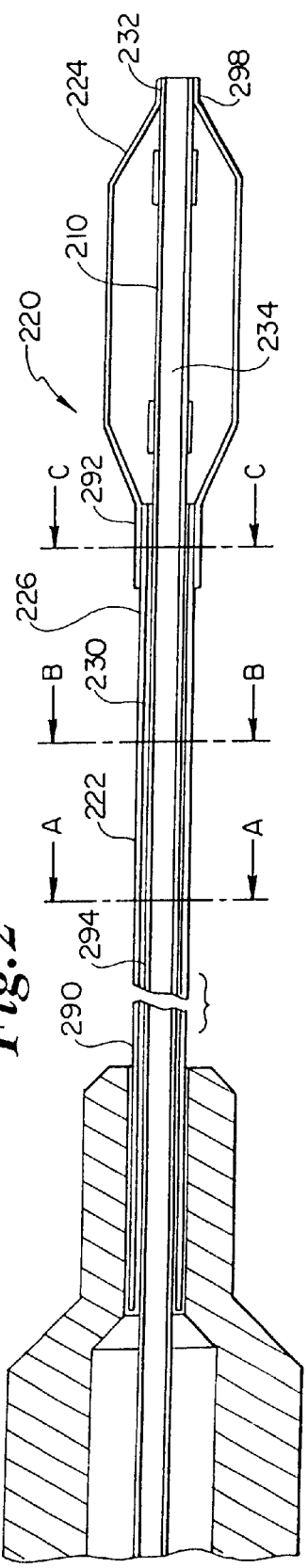
*Fig.1*
*Fig.3A*
*Fig.3B*
*Fig.3C*
*Fig.2*

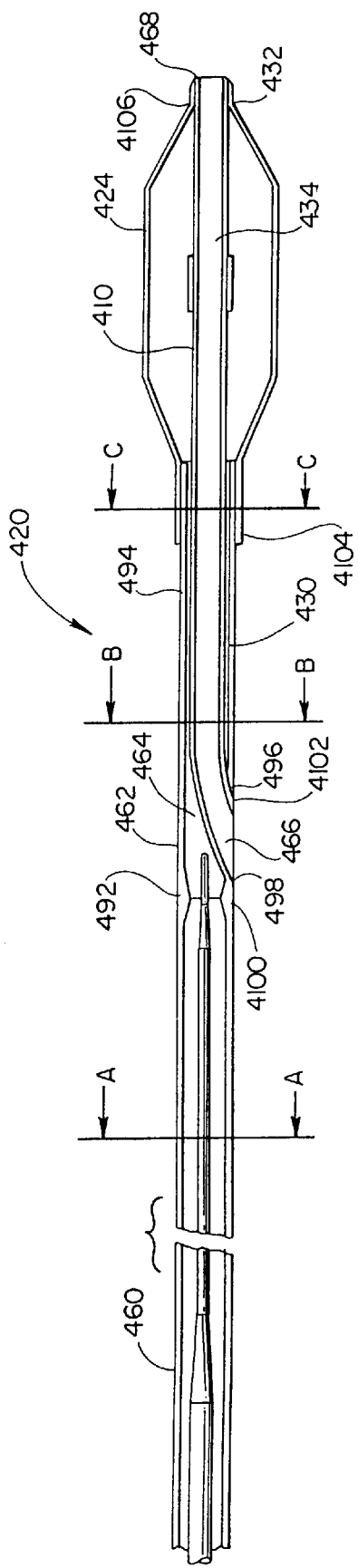
*Fig.4*
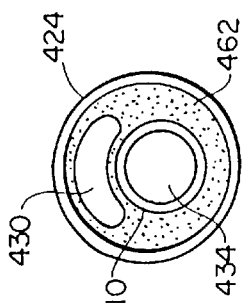
*Fig.5C*
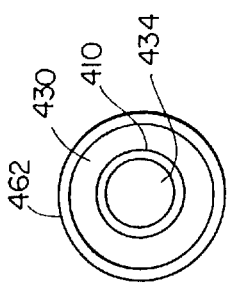
*Fig.5B*
*Fig.5A*

TRILAYER, EXTRUDED MEDICAL TUBING AND MEDICAL DEVICES INCORPORATING SUCH TUBBING

This application is a continuation 09/014,789 filed Jan. 28, 1998 of U.S. Pat. No. 6,165,166, which claims priority to Provisional Application Ser. No. 60/044,879, filed Apr. 25, 1977.

FIELD OF THE INVENTION

The present invention pertains generally to medical tubing and medical devices incorporating such tubing. More specifically, the present invention pertains to medical tubing and corresponding medical devices adapted for percutaneous transluminal use, such as guide catheters, diagnostic catheters such as illustrated in U.S. Pat. No. 5,403,292, and balloon catheters such as illustrated in U.S. Pat. No. 4,762,129. Medical tubing of the present invention is particularly useful to structurally define the lumen of a catheter, e.g., a rapid-exchange balloon catheter or an over-the-wire catheter. The tubing of the present invention is also useful as an inner member in a stent delivery device.

BACKGROUND OF THE INVENTION

Intravascular catheters are presently in wide clinical use for a variety of diagnostic and therapeutic purposes. Intravascular catheterization therapies, such as angioplasty, atherectomy, and laser irradiation, have been developed as alternatives to bypass surgery for treating vascular diseases or other conditions that occlude or reduce the lumen size of portions of a patient's vascular system. In particular, balloon angioplasty has proven to be a useful, and in many circumstances, a preferred treatment for obstructive coronary diseases. Also, intravascular diagnostic catheters for angiographics, ultrasonic imaging, and Doppler blood flow measurements for example, have been developed to measure or image the extent of the occlusion of a vessel, (e.g., stenosis). These intravascular diagnostic catheters may be used in conjunction with the aforementioned therapeutic catheters or may be used in conjunction with more invasive techniques such as coronary surgery. Intravascular therapeutic and diagnostic catheters have achieved acceptance because of their effectiveness as well as the fact that their use typically involves a relatively minor surgical procedure as compared to coronary bypass surgery.

However, the effectiveness of the techniques employing these catheters may at times be dependent upon the positioning of the catheter into the vascular system of a patient via an incision at an accessible location which may be remote from the site of occlusion or stenosis. Typically, for example, the intravascular catheter may be introduced into the femoral artery through an incision at the groin and then advanced through the femoral artery to the desired distal coronary site. Because of the small size of some of these vessels and the tortuous passages through the vessels, positioning of a catheter through a patient's vasculature can be a difficult and time consuming task. Furthermore, the catheters must be able to traverse these tortuous pathways in a manner as atraumatic to the patient as possible. Therefore, in order to limit insertion time and discomfort to the patient, intravascular catheters will preferably have several performance characteristics.

First of all, an intravascular catheter should exhibit good torque control such that manipulation of a proximal portion of the catheter is responsively translated to the tip or distal portion of the catheter. Moreover, the catheter should have sufficient strength in the longitudinal direction so as not to kink or fold as it is advanced through the vascular system. Also, for some types of intravascular catheters, it is desirable to maximize the inner diameter relative to the outer diameter, i.e., to make the lumen as large as practically possible. Specifically, for example, diagnostic catheters generally possess a relatively large lumen to allow fluids, such as radiopaque contrast fluid, to be injected therethrough and out the distal end so that the area of the vascular system under investigation can be viewed fluoroscopically.

Additionally, if the catheter is a dilation catheter, the outer surface of the tubing to be used in an intravascular catheter must be bondable to balloon material. Although the tubing may be bonded to the balloon with adhesive, this is not optimal as the adhesive may fail. Additionally, the adhesive undesirably adds to the surface profile of the catheter. Thus, it is preferable that the outer surface of the tubing of the catheter be directly bondable to the balloon material, such as by fusion bonding, described in U.S. Pat. Nos. 5,501,759 and 5,267,959.

Finally, catheter balloons are now being inflated to higher pressures than has been previously conventional in the art. For example, until recently, balloon inflation pressures typically averaged approximately 12 atmospheres. However, one current trend involves inflating balloons to pressures as high as 28 atmospheres. This relatively high pressure tends to stretch and constrict tubing if the tubing is too weak. In severe cases, the tubing could rupture. Thus, in order to be useful in a balloon catheter involving higher pressures, the tubing must be strong enough to withstand this higher pressure without collapsing or rupturing.

The internal lumen surface of intravascular catheters is subject to performance demands as well. For example, an important function of the internal lumen surface of intravascular catheters is to provide very low surface friction between the catheter and a guidewire and/or treatment device slidably engaging the lumen surface. The low friction internal surface facilitates advancement of the catheter over the guidewire or the advancement of the treatment device through the catheter lumen, as the case may be. Lubricity is especially critical in the curved portion of guide catheters. The low friction internal surface has typically been provided by the use of a lubricious polymer, e.g., polytetrafluoroethylene or the like, as the internal surface material, or alternatively, by coating the internal lumen surface of the catheter with a friction reducing material, such as liquid silicone.

In sum, catheter tubing should possess a combination of the desired characteristics of strength, pushability, torqueability, bondability and lubricity. However, such a combination of characteristics has not been achieved satisfactorily with tubing comprising only a single material. First of all, medical tubing formed from an inherently lubricious polymer tends to be difficult to effectively bond to the material of conventional balloons due to the chemical incompatibility between the materials to be bonded. On the other hand, polymer materials that demonstrate good bonding characteristics with balloons typically must be coated with a lubricant on the interior surface so that the interior surface is sufficiently lubricious, necessitating an additional manufacturing step. Furthermore, such lubricants tend to wear off, so that lubricity is diminished over time.

The prior art also describes several attempts to provide the desired characteristics by utilizing multilayered tubing in intravascular catheters. Conventionally, such multilayered tubing comprises an outer layer of a bondable material such as nylon, polyethylene, polyurethane, or poly(ethylene terephthalate) and an inner layer of a lubricious material such as polytetrafluoroethylene (PTFE) or other lubricious polymer, e.g., high density polyethylene. For example, U.S. Pat. No. 5,538,510 describes a coextrudable, flexible tubing which comprises an outer layer and an inner layer, the two layers being different materials and being covalently bonded to each other. Specifically, the patent purports to provide a length of tubing with the desired combination of properties by using a lubricious polymer as the inner layer, and a stiff polymer as the outer layer. The patent discloses that the flexible tubing is coextrudable and, furthermore, that the lumen of the tubing is sufficiently lubricious so as to obviate the use of a separate low friction sleeve and/or coating. Additionally, U.S. Pat. No. 4,707,389 describes a multi-layered tube composed of an outer layer of ethylenevinylacetate (EVA) and an inner layer of polyvinychloride (PVC), bonded together by a bonding layer. Finally, U.S. Pat. No. 3,561,493 discloses a multi-layered tubing in which the inner and outer layers are welded together by a precompounded layer of the two different polymers.

Although each of these patents purport to provide tubing and/or medical devices with the desired characteristics, problems still remain with existing multilayer tubing structures. For example, the low friction polymeric materials capable of providing a sufficiently lubricious lumen are generally chemically incompatible with the polymeric materials that are capable of providing adequate performance as the catheter outer layer. As a result of this chemical incompatibility, these different classes of materials do not form significant bonds with each other, even upon coextrusion, and thus, tubing comprising layers of these dissimilar materials tends to be subject to delamination. Further, substantial differences between the mechanical properties of the two classes of polymer materials further exacerbates this incompatibility problem.

There is thus a need in the art for medical tubing and medical devices incorporating such tubing that exhibit the desired characteristics of strength, pushability, torqueability, bondability and lumen lubricity. These and other objects are accomplished by the present invention, as hereinafter described.

SUMMARY OF THE INVENTION

According to the present invention, the above objectives and other objectives apparent to those skilled in the art upon reading this disclosure are attained by the present invention which is drawn to trilayered tubing as well as to a medical device suitable for percutaneous transluminal use comprising the tubing. More specifically, it is an object of the present invention to provide coextruded, flexible, trilayered tubing, wherein the three layers are firmly bonded together such that the layers resist delamination under operating conditions both normal and extreme (e.g., high balloon pressures of up to 28 atmospheres or more) and furthermore, wherein the materials that comprise the three layers provide the tubing with the desirable characteristics for tubing that is to be used in a medical device suitable for percutaneous transluminal use.

Generally, the present invention provides a length of coextruded, flexible tubing that meets the needs and objectives described hereinabove, by virtue of a multilayer structure. Specifically, the multilayer structure comprises a core layer of a lubricious polymeric material, an outer layer comprising directly bondable (defined below) polymer, and an intermediate tie layer comprising a polymer having pendant functionality capable of adhering the lubricious material of the core layer to the directly bondable material of the outer layer. In this manner, the intermediate tie layer provides a strong connection between the core layer and the outer layer.

In preferred embodiments, the glass transition temperature ($T_g$) characteristics of the intermediate tie layer are selected to be inbetween those of the core layer and the outer layer. Specifically, it is preferred that the glass transition temperatures vary only gradually from the core layer to the outer layer in order to provide a stage-wise transition of mechanical characteristics from the material of the outer layer to the material of the core layer. Preferably, the glass transition temperature of each layer will be from 85% to 115% of the glass transition temperature of the material(s) adjacent to it. By providing a gradient in the $T_g$ from the core layer to the outer layer, a more stable, more compatible, trilayered tubing is provided that possesses the desired characteristics of strength, pushability, torqueability, bondability, and a lubricious lumen, while also demonstrating dramatically improved resistance against delamination.

The present invention thus provides a length of coextruded, flexible tubing comprising an outer layer having a first glass transition temperature, an intermediate tie layer having a second glass transition temperature, and a core layer having a third glass transition temperature. Preferably, the first glass transition temperature is greater than the second glass transition temperature, which is preferably greater than the third glass transition temperature. Additionally, it is preferred that the outer layer be comprised of a material that is directly bondable to conventional balloon materials. It is further preferred that the core layer is comprised of a material that is lubricious and that the intermediate tie layer is comprised of a material that comprises functionality capable of adhering to both the material of the outer layer and the material of the core layer.

In another aspect, there is also provided a medical device suitable for percutaneous transluminal use comprising the tubing of the present invention and a radially expansive component operationally coupled to the tubing. For example, the tubing of the present invention may be utilized to define the guidewire lumen of a balloon catheter. More specifically, the trilayer tubing of the present invention may define the guidewire lumen of an over-the-wire catheter, i.e., where the guidewire lumen as defined by the trilayered tubing runs the entire length of the catheter. The tubing of the present invention may also define the guidewire lumen of a rapid exchange catheter, i.e., wherein one end of the guidewire lumen as defined by the tubing of the present invention extends through the distal end of the catheter and the opposite end exits through an outer wall of the catheter. Additionally, the trilayered tubing of the present invention may be utilized to form the inner member of a stent-delivery device, wherein a stent is releasably mounted to the tubing of the present invention.

As used herein, the phrase "direct bond" (or "directly bondable") is meant to indicate a bond between two materials that requires no bonding substance, i.e, adhesive, interposed between the materials (or materials that are so bondable). Additionally, the term "lubricious" as applied to the materials herein is meant to indicate a material that has a kinetic coefficient of friction (steel on polymer) of less than about 0.5. As used herein, "elastomeric" is meant to indicate that property of a material that allows the material to be stretched to at least twice their original length and to recover its original shape partially or completely after the deforming force has been removed. "Glass transition temperature" or "$T_g$" as used herein and as is generally known to those of skill in the art, refers to that temperature at which an amorphous material changes from a brittle vitreous state to a plastic state and may be determined by Differential Scanning Calorimetry (DSC). Finally, as used herein, the phrase "acid-functional" is meant to indicate materials that have pendant acidic functional groups.

BRIEF DESCRIPTION OF THE DRAWINGS

The above mentioned and other advantages of the present invention, and the manner of attaining them, will become apparent and the invention itself will be better understood by reference to the following description of the embodiments of the invention taken in conjunction with the accompanying drawings, wherein:

FIG. 1 is an enlarged, cross-sectional view of one embodiment of tubing in accordance with the present invention;

FIG. 2 is a longitudinal sectional view of an over-the-wire angioplasty catheter in accordance with the present invention;

FIG. 3A is an enlarged, cross-sectional view taken along line A—A of FIG. 2;

FIG. 3B is an enlarged, cross-sectional view taken along line B—B of FIG. 2;

FIG. 3C is an enlarged, cross-sectional view taken along line C—C of FIG. 2;

FIG. 4 is a longitudinal sectional view of a rapid exchange angioplasty catheter in accordance with the present invention;

FIG. 5A is an enlarged, cross-sectional view taken along line A—A of FIG. 4;

FIG. 5B is an enlarged, cross-sectional view taken along line B—B of FIG. 4;

FIG. 5C is an enlarged, cross-sectional view taken along line C—C of FIG. 4;

DETAILED DESCRIPTION OF THE INVENTION

Figure 6:
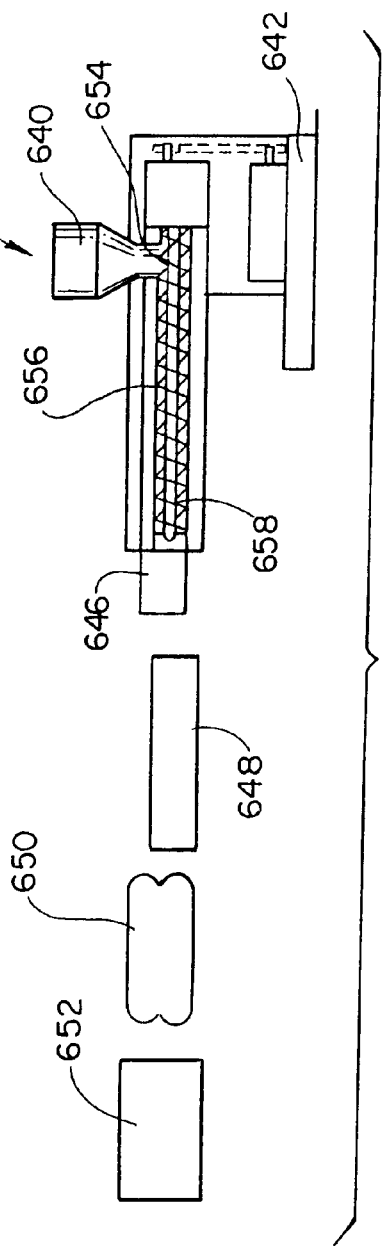
FIG. 6 is a schematic view of an extrusion system capable of extruding the tubing of the present invention.

The embodiments of the present invention described below are not intended to be exhaustive or to limit the invention to the precise forms disclosed in the following detailed description. Rather the embodiments are chosen and described so that others skilled in the art may appreciate and understand the principles and practices of the present invention.

According to the present invention, trilayer tubing 10 is illustrated in cross-sectional view in FIG. 1. In accordance with the present invention, tubing 10 comprises outer layer 16, intermediate tie layer 14, and core layer 12, the polymeric materials of the outer, tie and core layers typically being different and being formed preferably by coextruding. Inner surface 13 of trilayer tubing 10 defines lumen 15.

Outer layer 16 is preferably comprised of at least one directly bondable polymer. That is, outer layer 16 is preferably comprises of at least one polymer selected so as to be directly bondable to the balloon by a technique such as fusion bonding. A wide variety of polymers may be incorporated into outer layer 16. Preferably, the material chosen for use in outer layer 16 will be thermoplastic, so as to be more easily extrudable. It is further preferred that the material chosen for use in outer layer 16 will be elastomeric. Generally, preferred polymers for use in outer layer 16 have a weight average molecular weight in the range of from about 40,000 to about 100,000.

Outer layer 16 may preferably comprise a polyester, a polyamide or combinations thereof Exemplary polyesters which are suitable for use in outer layer 16 include polyesters containing both polyether and polyester segments. Particularly suitable are the family of polyether polyesters commercially available under the trade name Hytrel® from E.I. DuPont De Nemours and Company, Wilmington, Del. Also well-suited for use in outer layer 16 of tubing 10 of the present invention are the family of polyesters available under the trade name Arnitel® from DSM Engineering Plastics, Evansville, Ind.

Polyamides suitable for use in outer layer 16 in tubing 10 of the present invention include Nylon 12, Nylon 6/6 or other nylon copolymers, as well as polyether block amides. An example of a commercially available polyamide suitable for use in outer layer 16 in the tubing 10 of the present invention is available under the trade name PEBAX® from Atochem Inc., Glen Rock, N.J.

Core layer 12 is preferably made of at least one lubricious polymeric material to facilitate the advancement over a guidewire or advancement of a separate, smaller catheter through lumen 15 of tubing 10. Although it is preferred that core layer 12 be sufficiently lubricious without such a coating, a solid or liquid lubricant may coat the surface of lumen 15 as structurally defined by core layer 12, and thus such a coating is understood to be within the scope of the present invention. As discussed hereinabove, lubricious materials, as used herein, preferably are those materials with a kinetic coefficient of friction (steel on polymer) of less than about 0.5. Generally, preferred lubricious polymers have a weight average molecular weight in the range of from about 80,000 to about 300,000.

As representative examples, the at least one lubricious polymeric material incorporated into core layer 12 may preferably be selected from an olefinic polymer, a fluorinated polymer, or combinations thereof More preferably, the material of core layer 12, if an olefinic polymer, may comprise a high density polyethylene, an ultra high density polyethylene, a low density polyethylene, a linear low density polyethylene, or combinations thereof Such polyethylene resins are commercially available from the Quantum Chemical Company, Cincinnati, Ohio, under the trade name Petrothene® LS 5060-00 and LM 6007-00. Additional materials that are believed to be suitable in core layer 12 include fluorinated polymers such as polytetrafluorethylene (PTFE) and polyvinylidenefluoride (PVDF). Because PVDF is much easier and practical to extrude than PTFE, PVDF is presently a more preferred fluoropolymer.

Intermediate tie layer 14 is interposed between outer layer 16 and core layer 12. preferably in a manner such that neither the inner or outer surface of intermediate tie layer 14 is exposed. Intermediate tie layer 14 is preferably made of a polymeric material comprising functionality capable of adhering outer layer 16 to core layer 12. In this manner, intermediate tie layer 14 aggressively links the two other layers together with a strong connection that resists delamination. Generally, preferred polymers for use in intermediate tie layer 14 have a weight average molecular weight in the range of from about 40,000 to about 250,000.

Additionally, due to the extreme difference in mechanical properties discussed above, intermediate tie layer 14 is preferably made of a material selected to have thermal characteristics, e.g., a glass transition temperature, inbetween those of core layer 12 and outer layer 16 so as to provide a step-wise transition in mechanical properties from the material of outer layer 16 to those of the material of core layer 12. Intermediate tie layer 14 thus operates to reduce the stresses that might otherwise be created as a result of the differing materials of outer layer 16 and core layer 12 if the intermediate tie layer 14 of the present invention were not used. By virtue of this relationship and the functionality of the material of the intermediate tie layer 14, layers 12, 14 and 16 are strongly adhered together in a manner resistant to delamination.

Thus, any polymer having a having functionality capable of adhering to both core layer 12 and outer layer 16 may be advantageously used as intermediate tie layer 14. Representative examples of such polymers include olefinic and other free radically polymerized polymers having one or more functional groups selected from carbon-carbon double bonds, vinyl esters, amine groups, acid groups such as —COOH, —SO₃H, —PO₃H, the salts of such acids, and the like, an anhydric moiety such as

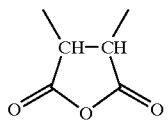

or combinations thereof, and the like.

For example, functionalized olefinic materials suitable for use in the intermediate tie layer 14 of tubing 10 include olefins such as polyethylene of varying densities, polypropylene, or polyethylene vinyl acetate that have been formed from olefinic monomers copolymerized with a copolymerizable monomer, e.g., maleic acid, having the desired functionality. Other unsaturated carboxylic acids such as fumaric acid, cinnamic acid, crotonic acid, linoleic acid, or the like may also be used as a substitute for maleic acid. These acid functional olefinic polymeric materials are described, for example, in U.S. Pat. No. 5,538,510, incorporated herein by reference.

Other examples of acid and anhydride functional polymers that are believed to be suitable for use in intermediate tie layer 14 include acid functional ethyl vinyl acetate resins, acid functional ethylene acrylate polymers, anhydride functional ethylene acrylate copolymers, anhydride functional ethyl vinyl acetate copolymers, acid and acrylate functional ethyl vinyl acetate resins, anhydride functional ethyl vinyl acetate copolymers, and anhydride functional ethyl vinyl acetate resins. In particular, suitable acid and anhydride functional polymers are commercially available under the trade name of Bynel® from E.I. DuPont De Nemours, Wilmington Del.

Functionalized polyethylenes are also suitable for use in intermediate tie layer 14. Examples of other such functionalized polyethylenes which are suitable for use in intermediate tie layer 14 include, but are not limited to, functionalized high density polyethylene and functionalized linear low density polyethylene. Such functionalized polyethylenes are commercially available from the Quantum Chemical Corporation under the trade name of Plexar®.

Additionally, the material of intermediate tie layer 14 may be a free radically polymerized copolymer of monomers comprising ethylene and an alkyl (meth)acrylate. Ethylene-methyl (meth)acrylate copolymers having ester functionality that are believed to be suitable as intermediate tie layer 14 are commercially available under the trade name EMAC® (e.g., EMAC® SP 2205 and 2260) from Chevron Company, Houston, Tex.

As mentioned hereinabove, the polymeric materials of the outer, core and intermediate tie layers 16, 12, and 14, respectively, are preferably comprised of materials with glass transition temperatures that are substantially similar so as to facilitate coextrusion and to help reduce the tendency of undue stress to build between the layers in the resultant tubing. Preferably, the glass transition temperature ($T_g$) of each layer will be from 85% to 115% of the glass transition temperature of the material(s) adjacent to it. In preferred embodiments, the $T_g$ of the functionalized polymer of intermediate layer 14 is about 1 to 1.15 times greater than the polymer of outer layer 16, and the $T_g$ of the lubricious polymer in core layer 12 is about 1 to 1.15 times greater than the functionalized polymer of intermediate tie layer 14.

Representative combinations of materials suitable for use in tubing 10 of the present invention are shown in Table 1, hereinbelow.

TABLE 1

| Core Layer (12) | Intermediate Tie Layer (14) | Outer Layer (16) |
|---|---|---|
| polyethylene | functionalized polyethylene | polyester |
| polyethylene | functionalized polyethylene | polyamide |
| polyethylene | ethylene-methyl acrylate copolymers | polyester |
| polyethylene | ethylene-methyl acrylate copolymers | polyamide |
| polyethylene | acid/anhydride functionalized vinylic copolymer | polyester |
| fluorinated polymer | functionalized polyethylene | polyester |
| fluorinated polymer | functionalized polyethylene | polyamide |
| fluorinated polymer | ethylene-methyl acrylate copolymers | polyester |
| fluorinated polymer | ethylene-methyl acrylate copolymers | polyamide |
| fluorinated polymer | acid/anhydride functionalized vinylic copolymer | polyester |

The thicknesses of layers 12, 14 and 16 will vary depending upon desired applications. For example, when used to define the guidewire lumen of an angioplasty catheter, the core layer 12 of tubing 10 will preferably have a thickness of from about 0.01 to about 0.05, while the intermediate tie layer 14 is preferably of a thickness of from about 0.006 to about 0.03 and outer layer 16 is preferably from about 0.01 to about 0.05 thick. More preferably, core layer 12 will be from about 0.01 to about 0.04 thick, intermediate tie layer 14 will be from about 0.003 to about 0.03 and outer layer 16 will be from about 0.01 mm to about 0.04.

Additionally, the diameter of tubing 10 will vary depending upon the end-use application. Typically, the overall, or outside, diameter ($D_o$) is typically between 0.5 and 0.7, and will preferably be from about 0.55 to about 0.63 mm. Core layer 12 will preferably define a lumen, such as a lumen adapted to receive a guidewire. The inside diameter ($D_i$) of the lumen so formed is typically from about 0.4 mm to about 0.6, and will preferably be from about 0.43 to about 0.51.

The tubing of the present invention may be used, for example, in medical devices suitable for percutaneous transluminal use, such as guide catheters, diagnostic catheters, or those medical devices in which a radially expansive component is to be therapeutically deployed, e.g., stent delivery devices or balloon catheters. In one embodiment of the invention, for example, the tubing of the present invention may be utilized to define a guidewire lumen in an over-the-wire balloon catheter 220, as illustrated in FIGS. 2 (where the balloon is illustrated in its deployed state), 3A, 3B and 3C. As illustrated, catheter 220 comprises an outer catheter tubing 222 which connects with balloon 224 at tubing distal end 226. Outer catheter tubing 222 terminates at its distal end 226, where outer catheter tubing 222 connects with the proximal end 292 of balloon 224. Outer catheter tubing 222 defines lumen 294.

The aforementioned connection, and any other connection, weld or bond mentioned herein, may be established by any method that forms fluid tight seals between the materials at the desired bond site, e.g., as with adhesive, or by direct bonding. However, it is generally preferred that these connections be established by direct bonding. Direct bonding is considered advantageous since the use of an intermediate adhesive layer is thereby avoided. The use of adhesive is a less desirable alternative as adhesive layers add to the thickness and rigidity of the medical device at the bond site. Additionally, many adhesives present biocompatiblity issues.

Thus, it is preferred that outer catheter tubing 222 is directly bonded to balloon 224 at distal end 226. These direct bonds may be established by any method known to those of ordinary skill in the art that effectively forms fluid tight seals between the materials to be bonded. For example, the direct bonds may be established by conductive, convective, or radiative heating, combinations thereof, of any one of these heating methods used in combination with pressure applied to the bond area. Furthermore, the direct bonds may be formed by fusion bonding. Fusion bonding using laser energy is disclosed in U.S. Pat. Nos. 5,267,959 and 5,501, 759; the disclosures of which are incorporated by reference herein.

Also, catheter 220 comprises an inner catheter tubing 210 which defines lumen 234. Inner catheter tubing 210 extends through lumen 294 of outer catheter tubing 222, thus defining a generally annular space 230 between outer catheter tubing 222 and inner catheter tubing 210. Generally, annular space 230 extends along the catheter 220 between outer catheter tubing 222 and inner catheter tubing 210, to terminate in communication with the interior 296 of balloon 224. Inner catheter tubing 210, however, extends through balloon 224 as shown in FIG. 1, being bonded to balloon 224 at distal end 232 in such a manner that the lumen 234 of inner catheter tubing 210 is open at distal end 232. Advantageously and preferably, distal end 298 of inner catheter tubing 210 is directly bonded to balloon 224 at distal end 232.

Although inner catheter tubing 210 is in the form of trilayer tubing of the present invention as described hereinabove with respect to FIG. 1, the three layers have not been individually illustrated in FIG. 2 for purposes of clarity. As previously stated, the material of the core layer 12 (illustrated in FIG. 1) preferably comprises a lubricious material that defines a lubricious inner lumen. By providing a lubricious inner lumen, the advancement of catheter 220 over a guidewire or the advancement of a separate, smaller catheter, for example, through lumen 234 of tubing 210 is facilitated.

Because of the lubricious nature of the polymer of the core layer 12, the polymer that is to comprise outer layer 16 may be selected to optimize other characteristics of catheter 220 rather than to provide the necessary lubricity to the inner lumen of catheter 220. For example, the polymer of outer layer 16 may be chosen on the basis of bondability to the desired balloon material. In preferred embodiments, at least a portion of the monomeric segments of the polymer of outer layer 16 correspond to at least a portion of the monomeric segments of the desired balloon material. For example, if outer layer 16 comprises a polyether polyester, i.e. a polymer comprising polyester and polyether segments, it would be preferred that the balloon comprise a material with polyether or polyester segments, such as polyethylene pterphthalate (PET).

In a second embodiment of the present invention, the trilayer, medical tubing of the present invention may be used as the inner catheter tubing 410 in a rapid exchange balloon catheter 420, as illustrated in FIGS. 4, 5A, 5B, and 5C. Again, although inner catheter tubing 410 is in the form of trilayer tubing of the present invention as described hereinabove with respect to FIG. 1, the three layers have not been individually illustrated in FIG. 4 for purposes of clarity.

Catheter 420 comprises a tubular proximal shaft 460, a tubular stem 462, inner catheter tubing 410 and a balloon 424. Stem 462 is in fluid communication with proximal shaft 460 and is bonded to the distal end 492 of proximal shaft 460. Inner catheter tubing 410 defines guidewire lumen 434. Inner catheter tubing 410 extends from distal portion 492 of proximal shaft 460 and through lumen 464 of stem 462, beyond the distal end 494 of stem 462, and through balloon 424. Inner catheter tubing 410 additionally comprises a proximal end 496 open to the outside of the catheter 420 at skive 466. Inner catheter tubing 410 and stem 462 are preferably directly bonded together at weld 4102 proximal to balloon 424. At the skive 466, the distal end 492 of proximal shaft 460, the proximal end 496 of tubular stem 462, and the proximal end 4100 of inner catheter tubing 410 are directly bonded together. Inner catheter tubing 410 is off-center at skive 466 but becomes approximately centered throughout the remaining length of stem 462. Balloon 424 is arranged coaxially around inner catheter tubing 410 with the proximal neck 4104 of balloon 424 directly bonded to the distal end of stem 462 at the outer surface thereof The distal neck 432 of balloon 424 is directly bonded to the distal end 4106 of inner catheter tubing 410, together forming the catheter tip 468.

Figure 7:
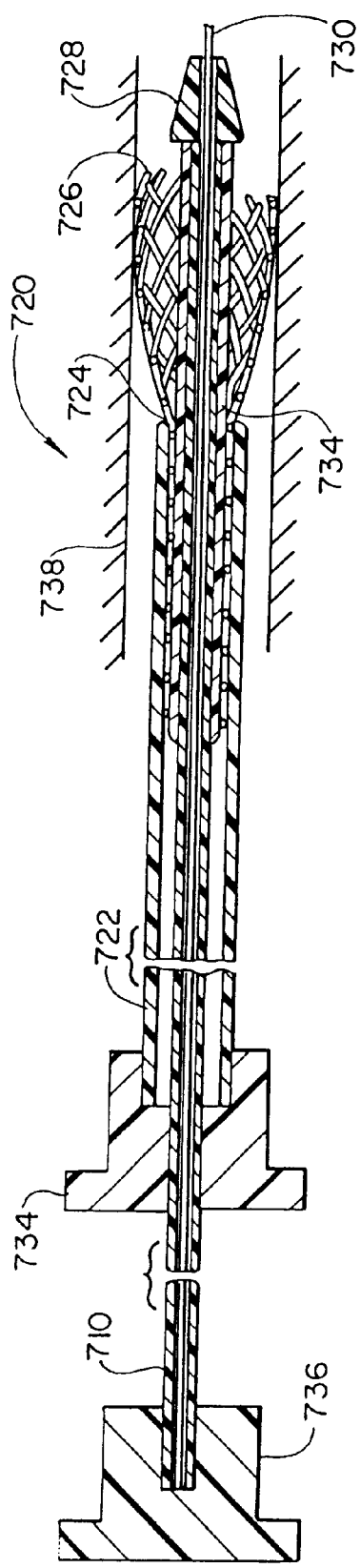
FIG. 7 is a longitudinal sectional view of a stent delivery device in accordance with the present invention
Figure 6:
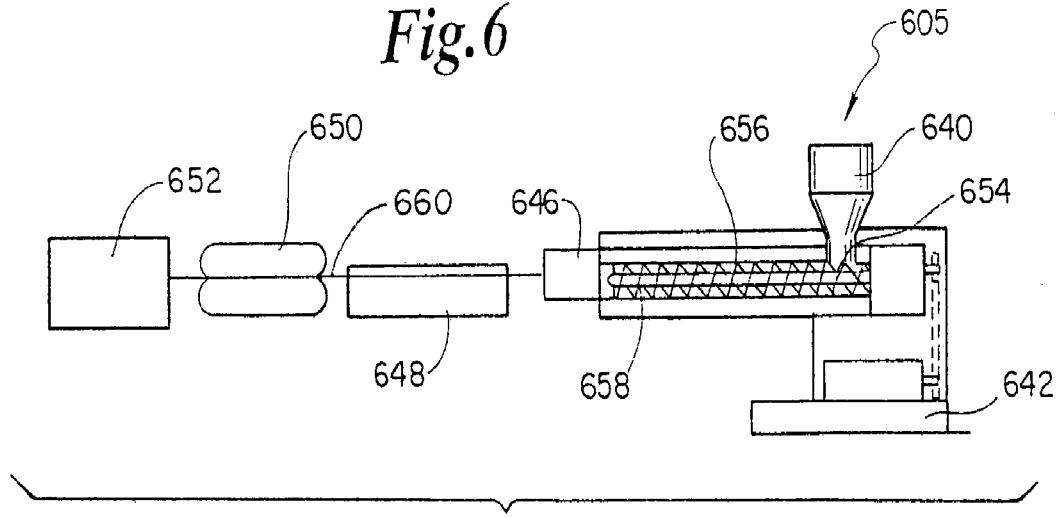

In a third embodiment of the present invention, the tubing of the present invention may be used as the inner member 710 in a stent delivery device, as illustrated in FIG. 7, in which the stent is illustrated in its deployed state. As was the case with FIGS. 2 and 4, although inner catheter tubing 710 is in the form of trilayer tubing of the present invention as described hereinabove with respect to FIG. 1, the three layers have not been individually illustrated in FIG. 7 for purposes of clarity.

Stent delivery device 720 comprises a tubular outer sleeve 722 and a hollow, flexible core element 710. Outer sleeve 722 has integral handle 734 attached at its proximal end. The distal end 724 of outer sleeve 722 is positioned within a body canal 738. Disposed axially within outer sleeve 722 is hollow, flexible core element 710 having a handle 736 at its proximal end. The distal end 728 of the core element 710 has a stepped up diameter where it meets the distal end 724 of outer sleeve 722 so that it provides a smooth transition at the distal end 724 of outer sleeve 722, and is also located within body canal 738. A guide wire 730 passes axially through the hollow core. Attached around the periphery of the core element 710 at its distal end 728 is grip member 732 which releasably grips a self-expanding stent 726 (shown partly deployed).

The tubing 10 of the present invention can be manufactured by coextrusion as schematically illustrated in FIG. 6. Although three extruders typically are used, one for each layer 12, 14 and 16, only one extruder 605 is shown for purposes of clarity. In the case of such trilayer extrusion, the three desired materials can converge through one die 646 to create a single trilayer tube. Referring to the operation of extruder 605, which is representative of all three extruders, pellets (not shown) of suitable material can be gravitationally fed from a hopper 640 into the feed section 654 of extruder 605. There, the pellets come into contact with rotating screw 656. The pellets are then conveyed through barrel 658 by rotating screw 656. The pellets are heated by electrically heated barrel 658 and by the frictional and shear action of the screw 656 as it turns in the barrel 658. Eventually, as the pellets move down the length of the barrel 658, the pellets are transformed into a molten phase which is then forced out of a coextrusion die 646 along with molten material from the other two extruders to create a coextruded tube 660. The tube 660 is then drawn down into cooling trough 648 to cool and set the tube 660 into a predetermined thickness and diameter by means of puller 650. Once the tube 660 is cooled and pulled it is ready for collection, i.e., with a cutter (not shown) or coiler 652, and use.

For example, the extrusion line may comprise the following equipment:

2 ¾" Davis Standard Extruder (for inner and outer layers)
1 ½–¾" Davis Standard Extruder (for middle layer)
1 3-layer Genca Crosshead (tri-die, commercially available from Genca Extrusion Technology, Clearwater, Fla.)
1 Water Bath
1 Puller RDN
1 Laser gauge Zumbach (to check dimensions).

Process conditions include:

| | |
|---|---|
| Temperatures | 370°–470° F. |
| Pressures | 1000–3000 psi |
| Line Speed | 50–200 fpm |

The following examples, while not intended to be limiting, illustrate various features of the present invention.

EXAMPLE 1

The following experiment was performed to investigate the effects of irradiation sterilization on an HDPE layer of trilayer tubing.

Specifically, one hundred pieces of 6" tubing made of Hytrel® 63D as the outside layer, Plexar® 209 as the middle layer, and HDPE 6007 as the inside layer were irradiated (0.0185" overall ID×0.0265" overall OD). Twenty pieces were irradiated at dosages of 20 Mrad, 30 Mrad, 40 Mrad, 50 Mrad, and 60 Mrad, respectively. Control samples receiving no irradiation were also provided.

Differential Scanning Calorimetry (DSC) was used to determine the thermal properties of the three different layers. No significant differences were seen between control samples or samples at any of the dosage levels.

Solids rheology testing was also performed with similar conclusions. No significant changes were detected between the samples at any of the dosage levels.

To test the effect of the irradiation on the bondability of the outer surface of the tubing to balloon material, PET balloons were bonded to the tubing by fusion bonding and then the bond site skived and inspected for delamination. No significant differences in the amount of delamination were noted between any of the dosage levels and the control.

It was concluded that irradiating with electron-beam irradiation the trilayer tubing does not adversely affect resistance to delamination nor does irradiation increase the melt resistance of the HDPE layer.

EXAMPLE 2

Tests were performed to determine if trilayer tubing can be effectively laser-bonded to angioplasty balloons comprising polyethyleneterphthalate (PET) as an inner balloon layer. Trilayer tubing having an inner diameter (ID) of 0.0182 inches and an outer diameter (OD) of 0.0236 inches and including Hytrel® 7246 as the outside layer, Plexar® 209 as the middle layer, and HDPE 5006 as the inside layer, was tested.

The outer layer of the tubing was fusion bonded to PET of balloon using laser energy as described in Forman, U.S. Pat. No. 5,501,759. Weld spot size was held constant at 2.215 inches and RPM was held constant at 2500. Power was varied between 2.0, 3.0, and 4.0 Watts, respectively.

It was concluded that effective bonds were achieved at all power levels. No bonds failed before balloon burst occurred. Also, times for proximal and distal bonds were set for each power level, despite the variation in wall thickness between parts. The best bonds were achieved with the 3.0 Watt power setting, based on visual examination after burst.

EXAMPLE 3

Crush tests were performed on tubing of the present invention made of Hytrel® 7246 as the outside layer, Plexar® 209 as the middle layer, and HDPE 6007 as the inside layer.

| | | Start Pressure: 147.0 (10 ATM) Increment: 14.7 PSI | | Stop Pressure: 411.6 (28 ATM) Hold Time: 15 seconds | | | |
|---|---|---|---|---|---|---|---|
| | | RESISTANCE | LOCKS | DAMAGE | AFTER INFLATION TO 28 ATM | | |
| ID" | OD" | FELT AT: | UP AT: | OBSERVED | AVG OD" | MIN. OD" | MAX OD" |
| 0.0169 | 0.0225 | 352.8 (24 ATM) | Does Not Lock | No Damage | 0.0226 | 0.0224 | 0.0227 |
| 0.0169 | 0.0224 | 367.5 (24 ATM) | Does Not Lock | No Damage | 0.0227 | 0.0226 | 0.0228 |
| 0.0172 | 0.0232 | 352.8 (24 ATM) | Does Not Lock | No Damage | 0.0231 | 0.0228 | 0.0234 |
| 0.0169 | 0.0226 | 382.2 (26 ATM) | Does Not Lock | No Damage | 0.0228 | 0.0226 | 0.0229 |
| 0.017 | 0.0227 | 367.5 (25 ATM) | Does Not Lock | No Damage | 0.0228 | 0.0225 | 0.023 |

-continued

| | | | | | | | |
|---|---|---|---|---|---|---|---|
| Start Pressure: 147.0 (10 ATM) | | | | Stop Pressure: 411.6 (28 ATM) | | | |
| Increment: 14.7 PSI | | | | Hold Time: 15 seconds | | | |
| | | RESISTANCE | LOCKS | DAMAGE | AFTER INFLATION TO 28 ATM | | |
| ID" | OD" | FELT AT: | UP AT: | OBSERVED | AVG OD" | MIN. OD" | MAX OD" |
| x = .0170 | x = .023 | x = 364.56 | | | x = .0228 | x = .0226 | x = .0230 |
| s = .0001 | s = .0003 | s = 12.30 | | | s = .0002 | s = .0001 | s = .0003 | x = mean.
s = standard deviation.

"Resistance felt" means the point when the tube collapsed enough so that an increase in friction was felt on a guidewire by an operator pulling it through the tubing. "Locks up" is meant to indicate the point at which the guidewire is completely stuck due to the collapse of the tube.

EXAMPLE 4

Crush tests were performed on tubing of the present invention made of Hytrel® 7246 as the outside layer, Plexar® 209 as the middle layer, and HDPE 6007 as the inside layer.

| | | | | | | | |
|---|---|---|---|---|---|---|---|
| Start Pressure: 147.0 (10 ATM) | | | | Stop Pressure: 411.6 (28 ATM) | | | |
| Increment: 14.7 PSI | | | | Hold Time: 15 seconds | | | |
| | | RESISTANCE | LOCKS | DAMAGE | AFTER INFLATION TO 28 ATM | | |
| ID" | OD" | FELT AT: | UP AT: | OBSERVED | AVG OD" | MIN. OD" | MAX OD" |
| 0.0169 | 0.0228 | 367.5 (25 ATM) | 470.4 (32 ATM) | Slightly Oval | 0.0228 | 0.0224 | 0.0232 |
| 0.0168 | 0.0232 | 382.2 (26 ATM) | 470.4 (32 ATM) | Slightly Oval | 0.0228 | 0.0226 | 0.023 |
| 0.0171 | 0.0235 | 382.2 (26 ATM) | 470.4 (32 ATM) | Slightly Oval | 0.0232 | 0.0225 | 0.0235 |
| 0.0168 | 0.0227 | 367.5 (25 ATM) | 455.7 (31 ATM) | Slightly Oval | 0.0226 | 0.0222 | 0.023 |
| 0.0171 | 0.023 | 367.5 (25 ATM) | 470.4 (32 ATM) | Slightly Oval | 0.0228 | 0.0223 | 0.0231 |
| x = .0169 | x = .023 | x = 373.38 | x = 467.46 | | x = .0228 | x = .0224 | x = .0232 |
| s = .0002 | s = .0003 | s = 8.05 | s = 6.57 | | s = .0002 | s = .0002 | s = .0002 | x = mean.
s = standard deviation.

"Resistance felt" and "lock-up" have the same meanings as in Example 3.

EXAMPLE 5

Tests were performed to determine the tensile strength effect of annealing at different temperatures and times for 0.0185" ID×0.0235" OD trilayer tubing. Material composition of the tubing is Hytrel® 7246 as the outside layer, Plexar® 209 as the middle layer, and HDPE 6007 as the inside layer. Five unannealed tubes of the same size were tested and found to have an average peak load of 1.255 lbs (standard deviation 0.047).

| Annealing time, temp | Peak Load lb. | Peak Stress psi | % Strain @ Break % | Yield Stress psi | % Strain @ yield % | Modulus psi |
|---|---|---|---|---|---|---|
| 1 hr., 100° C. | 1.4 | 8451.5 | 367.8 | 4578.1 | 11.724 | 93329 |
| 4 hr., 100° C. | 1.4 | 8520.7 | 368.9 | 4665.5 | 11.273 | 99734.7 |

-continued

| Annealing time, temp | Peak Load lb. | Peak Stress psi | % Strain @ Break % | Yield Stress psi | % Strain @ yield % | Modulus psi |
|---|---|---|---|---|---|---|
| 2.5 hr., 110° C. | 1.4 | 8728.6 | 385.7 | 4710.7 | 11.694 | 96051.8 |
| 1 hr., 120° C. | 1.5 | 9041.8 | 389.2 | 4885.3 | 12.682 | 96250.6 |
| 4 hr., 120° C. | 1.6 | 9421.3 | 382.3 | 4954.6 | 12.131 | 96887.6 |

EXAMPLE 6

A test was performed on 10 pieces measuring 0.0185" ID×0.0235" OD to check for shrinkage. The pieces were made of Hytrel® 7246 as the outside layer, Plexar® 209 as the middle layer, and HDPE 6007 as the inside layer. Parts were measured for i.d. with a mandrel, o.d. in two marked places, and length. They were annealed for 4 hours at 120°

C. and found to have no significant shrinkage in any parameter measured.

In sum, it has been found that medical tubing made according to the present invention allowed for good guidewire movement (with or without blood in lumen), traceability, ability to bend, crush resistance, kink resistance, low profile, good tensile strength, coatability, cost effectiveness, gamma stability, and biocompatability.

Other embodiments of this invention will be apparent to those skilled in the art upon consideration of this specification or from practices of the invention disclosed herein. Various omissions, modifications, and changes to the principles and embodiments described herein may be made by one skilled in the art without departing from the true scope and spirit of the invention which is indicated by the following claims. For instance, additional layers (e.g., a fourth layer) can be extruded inside of the inner layer or outside of the outer layer. All documents cited herein are incorporated by reference in their entireties for all purposes.

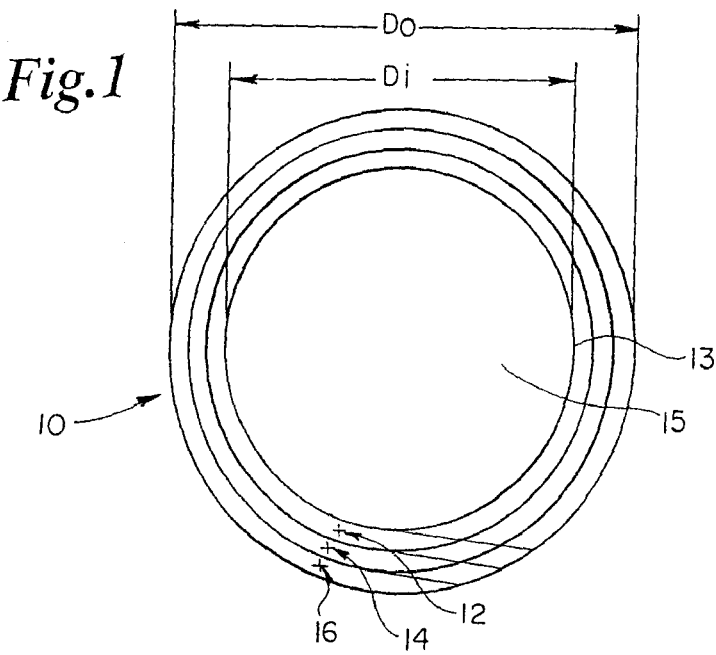

What is claimed is:

1. A co-extrusion of polymeric materials, the co-extrusion comprising:
    a first polymeric material having a first glass transition temperature;
    a second polymeric material having a second glass transition temperature, the second polymeric material further lacking a bonding affinity with the first polymeric material;
    an intermediate layer having a third glass transition temperature, the intermediate layer positioned between the first polymeric material and the second polymeric material, the intermediate layer further having a bonding affinity to both the first polymeric material and the second polymeric material; and
    wherein the glass transition temperatures for the first polymeric material, the second polymeric material, and the intermediate layer are within 85% to 115% of one another.

2. The co-extrusion of claim 1, wherein the co-extrusion is tubular in shape.

3. The co-extrusion of claim 2, wherein the first polymeric material defines a lumen of the tubular co-extrusion.

4. The co-extrusion of claim 1, wherein the second polymeric material is selected from a polyester, a polyamide, or combinations thereof.

5. The co-extrusion of claim 1, wherein the second polymer is a polyester.

6. The co-extrusion of claim 5, wherein the polyester comprises at least one polyether segment and at least one polyester segment.

7. The co-extrusion of claim 1, wherein the second polymer is a polyamide.

8. The co-extrusion of claim 1, wherein the first polymeric material is selected from an olefinic polymer, a fluorinated polymer or combinations thereof.

9. The co-extrusion of claim 8, wherein the olefinic polymer is selected from high density polyethylene, ultra high density polyethylene, low density polyethylene, linear low density polyethylene, or combinations thereof.

10. The co-extrusion of claim 8, wherein the fluorinated polymer is polyvinylidene fluoride.

11. The co-extrusion of claim 1, wherein the intermediate tie layer comprises a polymer selected from an anhydride modified olefinic polymer, an acrylate modified olefinic polymer, or combinations thereof.

12. The co-extrusion of claim 11, wherein the polymer of the intermediate tie layer is selected from a functionalized polyethylene, a functionalized vinylic polymer, a ethylene-methyl acrylate copolymer, an acid modified ethyl vinyl acetate polymer, an acid modified ethylene acrylate copolymer, an anhydride modified ethylene acrylate copolymer, an anhydride modified ethyl vinyl acetate copolymer, an acid modified ethyl vinyl acetate polymer, an acrylate modified ethyl vinyl acetate polymer, an anhydride modified ethyl vinyl acetate copolymer, an anhydride modified ethyl vinyl acetate polymer, or combinations thereof.

13. The co-extrusion of claim 12, wherein the polymer of the intermediate tie layer is selected from a functionalized polyethylene, a functionalized copolymer obtained from monomers comprising ethylene and alley (meth)acrylate, an anhydride modified ethyl vinyl acetate polymer, or combinations thereof.

14. A catheter shaft for percutaneous transluminal use, the catheter shaft comprising:
    an outer layer having a first glass transition temperature;
    a core layer defining a lumen extending the length therethrough, the core layer having a third transition temperature; and
    an intermediate tie layer disposed between at least a portion of the outer layer and the core layer, the intermediate tie layer having a second glass transition temperature; and
    wherein the first, the second and the third glass transition temperatures are within 85% to 115% of the glass transition of the layer or layers adjacent thereto.

15. The catheter shaft of claim 14, wherein the outer layer lacks a bonding affinity to the core layer.

16. The catheter shaft of claim 14, wherein the intermediate tie layer possesses a bonding affinity to both the outer layer and the core layer.

17. The catheter shaft of claim 14, wherein the catheter shaft further comprises a radially expansive component coupled to the catheter shaft.

18. The catheter shaft of claim 17, wherein the radially expansive component is a balloon.

19. The catheter shaft of claim 14, wherein the outer layer is selected from a polyester, a polyamide, or combinations thereof.

20. The catheter shaft of claim 14, wherein the core layer is selected from an olefinic polymer, a fluorinated polymer or combinations thereof.

21. A balloon catheter for percutaneous transluminal use, the balloon catheter comprising:
    a first tubular member having a lumen extending the length therein;
    a second tubular member coaxially disposed within at least a portion of the first tubular member with a distal segment extending distally beyond a distal end of the first tubular member, wherein the second tubular member comprises a core layer having a first glass transition temperature, an outer layer having a third glass transition temperature, and an intermediate tie layer disposed between at least a portion of the outer layer and the core layer, the intermediate tie layer having a second glass transition temperature, wherein the first glass transition temperature is greater than the second glass transition temperature, and the second glass transition temperature is greater than the third glass transition temperature, and further wherein the first glass transition temperature, the second glass transition temperature and the third glass transition temperatures are within 85% to 115% of the glass transition temperature of the layer or layers adjacent thereto; and a balloon having a proximal end, a distal end and an expandable region there between, wherein the distal end of the balloon is affixed to the distal segment of the second tubular member and the proximal end of the balloon is affixed to the first tubular member, and further wherein the expandable region of the balloon is in fluid communication with the lumen of the first tubular member.

22. The balloon catheter of claim 21, wherein the outer layer is selected from a polyester, a polyamide, or combinations thereof.

23. The balloon catheter of claim 22, wherein the core layer is selected from an olefinic polymer, a fluorinated polymer or combinations thereof.

* * * * *

UNITED STATES PATENT AND TRADEMARK OFFICE
CERTIFICATE OF CORRECTION

PATENT NO. : 6,464,683 B1
DATED : October 15, 2002
INVENTOR(S) : Christine M. Samuelson and Sarah J. Krieger It is certified that error appears in the above-identified patent and that said Letters Patent is hereby corrected as shown below:

<u>Title page,</u>
Item [54], Title, delete "TUBBING" and insert therefor -- TUBING --.

<u>Drawings,</u>
Sheet 1, Figure 1, the reference numeral -- 10 -- should be applied as shown on the attached page.
Sheet 3, Figure 6, the reference numeral -- 660 -- should be applied to a line that should be inserted as shown on the attached page.

Signed and Sealed this

Seventeenth Day of February, 2004

JON W. DUDAS
*Acting Director of the United States Patent and Trademark Office*